United States Patent
Gottschalk et al.

(10) Patent No.: US 6,676,947 B1
(45) Date of Patent: Jan. 13, 2004

(54) USE OF ERYTHROPOIETIN FOR THE TREATMENT OF HAEMOCHROMATOSES

(75) Inventors: René Gottschalk, Frankfurt am Main (DE); Paul Lehmann, Worms (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/647,642

(22) PCT Filed: Apr. 9, 1999

(86) PCT No.: PCT/EP99/02422

§ 371 (c)(1), (2), (4) Date: Oct. 3, 2000

(87) PCT Pub. No.: WO99/52542

PCT Pub. Date: Oct. 21, 1999

(30) Foreign Application Priority Data

Apr. 9, 1998 (DE) .......... 198 16 035
Jun. 18, 1998 (EP) .......... 98250222

(51) Int. Cl.[7] .......... A61K 38/00; A61K 38/17
(52) U.S. Cl. .......... 424/198.1; 514/2; 514/12; 424/602; 423/308
(58) Field of Search .......... 514/2, 8, 12; 424/602, 424/198.1; 423/308; 530/300

(56) References Cited

U.S. PATENT DOCUMENTS 4,992,419 A     2/1991  Woog et al.
5,603,943 A  *  2/1997  Yanagawa et al. .......... 424/434

FOREIGN PATENT DOCUMENTS

| EP | 0269394 | * 11/1987 |
| EP | 0 269 394 | 6/1988 |
| EP | 0 935 901 | 9/1999 |
| WO | WO 9639202 | * 12/1996 |

OTHER PUBLICATIONS

Jones–Lecointe, A., et al., Clin. Lab. Haemat., 13, pp. 251–253 (1991).
Massry S.G., Kidney International, 24, Suppl 16, pp. S–204–S–207 (1983).
Hutchison, F.N., et al. Americal Journal of Kidney Disease, 29, pp. 651–657 (1997).
Ureña, P. et al., Nephron, 59, pp. 384–393 (1991).

* cited by examiner

Primary Examiner—Karen Cochrane Carlson
Assistant Examiner—Samuel W. Liu
(74) Attorney, Agent, or Firm—George W. Johnston; John P. Parise

(57) ABSTRACT

The combination of erythropoietin and calcium, with or without phosphates, is useful for treating haemochromatoses. A method for treating primary haemochromatoses in a patient involves administering to the patient a combination therapy including an erythropoietin preparation and a calcium preparation, where the erythropoietin preparation and the calcium preparation are each administered from 1 to 5 times weekly. Beneficially, this combination therapy further administers a phosphorus preparation.

8 Claims, No Drawings

USE OF ERYTHROPOIETIN FOR THE TREATMENT OF HAEMOCHROMATOSES

This application is under 35 USC 371 based on PCT International Application No. PCT/EP99/0422, filed Sep. 4, 1999, which is an application claiming foreign priority of German application No. 198 16 035.6, filed Sep. 4, 1999.

The invention relates to use of erythropoietin (Epo) in low doses for production of pharmaceutical preparations for treatment of haemochromatoses and pharmaceutical combination preparations containing erythropoietin (Epo) and calcium compounds and/or phosphate compounds. These combination preparations are used particularly for treatment of primary haemochromatoses (inherited disturbances through excess of iron).

More than ⅔ (about 70%) of newly-formed bone-marrow parent cells in the organism participate in metabolism of iron and bone into erythrocytes and osteoblasts or osteoclasts. These processes (erythropoiesis and bone formation) are controlled by the two differentiating hormones, i.e. erythropoietin (Epo) and parathyroid hormone (PTH), the normal PTH concentration in the serum (between 10 and 60 ng/l) resulting in normal formation of osteoblasts and osteoclasts whereas normal concentrations of Epo, between 6 and 25 U/l, result in normal formation of erythrocytes.

Erythopoiesis in particular is vitally important, since 45% of newly-formed bone-marrow parent cells develop into erythrocytes. For this reason all parameters (iron resorption, iron incorporation, Epo, folate, vitamin B12) of the iron metabolism are extremely closely regulated.

As is known, Epo is a glycoprotein which is formed in the kidneys and can also be synthesised and stimulates blood formation (erythropoiesis) "humorally", i.e. by way of the bloodstream.

It is known to treat anaemia, particularly anaemia of haemodialysis patients caused by transfusion (renal anaemia) with recombinant human erythropoietin (rhEpo). Anaemia in chronic illness is the second most frequent form of anaemia throughout the world.

Reduced production of new erythrocytes is an important factor in anaemia when caused by reduced erythropoiesis in the bone or disturbances in iron re-utilisation. The daily iron requirement for normal erythropoiesis is 25 mg. Iron deficiency anaemia, which is the most frequent form of hypochromic anaemia, is regulated by addition of iron. Administration in combination with rhEpo is used in therapy in order to obtain a significant increase in the number of erythrocytes.

In clinical chemistry, disturbances in iron metabolism are diagnosed by determining the concentration of serum ferritin. The total body iron is about 3.5 g in men and 2.5 g in women. Iron occurs in active metabolism and in storage compartments. The active pool in a man on average contains 2100 mg in the haemoglobin, 200 mg in the myoglobin, 150 mg in enzymes in the tissue (haem and non-haem) and 3 mg in the iron transport compartment. Iron in the form of ferritin (700 mg) and haemosiderin (300 mg) is stored in tissue between the cells.

The total resorption mechanism for iron has not yet been fully explained (Gunshin et al., Nature 388, 482–488, 1997), but probably occurs via the protein divalent cation transporter ("DCT1"). Regulation is critically influenced by the small-intestine mucosa cells. In the case of the mucosa, the critical signal seems to be the total iron content of the body. It has been shown that the serum ferritin concentration is inversely related to the quantity of absorbed iron.

The iron is delivered by the intestinal mucosa cells to the transferrin. This iron transport protein has two iron-bonding sites. It is synthesised in the liver. There is therefore a mechanism whereby iron can be taken from cells (e.g. small-intestine mucosa or macrophages) and delivered to specific membrane receptors of erythroblasts, placenta cells or liver cells. Through endocytosis, the transferrin-iron-receptor complex arrives at the erythrocyte precursor cells, where the iron is delivered to the mitochondria, where haem is formed from iron and protoporphyrin.

Iron not needed for erythropoiesis is conveyed by transferrin to two kinds of storage pools. The most important store is ferritin. This is a heterogeneous family of proteins surrounding an iron nucleus. It is soluble and is the active storage form in the liver (hepacytes), bone marrow, spleen (macrophages), erythrocytes and in the serum (about 100 ng/ml). The tissue ferritin pool is very labile and quickly available when iron is needed. The circulating serum ferritin comes from the reticulo-endothelial system (RES) and the concentration in circulation varies in parallel with the total body iron (each ng/ml corresponds to 8 mg of iron supply).

To sum up, in iron metabolism all cells of the RES are stores of ferritin and haemosiderin, Hb-synthesising, iron-consuming parent cells are converted by Epo into erythrocytes and iron is transported by transferrin from the store to the erythrocytes in process of formation and back from dead erythrocytes into the store.

In bone metabolism, on analogy with iron metabolism the bone stores hydroxyl apatite crystals (and collagen) and the osteoclast "labilises" the hydroxyl apatite by breaking it down to a basic skeleton.

If no disturbance occurs, the basic skeleton is used for synthesis.

parent cells which synthesise hydroxyl apatite (and collagen) and consume calcium and phosphate are converted by PTH (+IGF 1+2) into osteoblasts and calcium and phosphate are transported from the store to the osteoblasts in process of formation and back to the store after synthesis of hydroxyl apatite.

As early as 1983, S. G. Massry (Kidney International 24, (16) 204–207) and also F. N. Hutchison and J. Jones (AJKD Vol. 29, No. 5, May 1997) described how in cases of hyperparathyroidism, i.e. at very high PTH concentrations, erythropoiesis is suppressed. In other words a high concentration of PTH (>>60 ng/l) slows down the formation of Epo in the organism, thus inevitably reducing the formation of erythrocytes.

PTH is therefore an important regulator in the human organism, since both iron metabolism and bone metabolism are regulated by PTH. PTH of course regulates resorption of calcium, phosphate, magnesium and iron.

However, the following weak points may occur in iron and bone metabolism:

insufficient differentiation of the parent cells by Epo or PTH,

"labilisation" of the form of storage (iron nucleus in ferritin or hydroxyl apatite in collagen by osteoclast) or insufficient transport of iron to erythrocytes or hydroxyl apatite (calcium and phosphate) to the osteoblasts.

Treatment is possible for disturbances of erythropoiesis in the case of renal anaemia or iron deficiency anaemia but no successful treatment has been found for haemochromatoses. Bloodletting is the only method at present.

Haemochromatoses are iron storage diseases resulting from an excess of iron in the organism, particularly in the parenchymatous organs, associated with increased iron absorption and massive deposition of iron in the form of haemosiderin in numerous organisms and in the monocyte-macrophage system. A distinction is made between primary (idiopathic) haemochromatoses and secondary (erythropoietic) haemochromatoses. Secondary haemochromatoses are disturbances in blood formation resulting in haemosiderosis (inherited excess of iron in the organism). Primary (idiopathic) haemochromatoses appear in the form of liver cirrhosis (pigment cirrhosis), bronze discoloration of the skin and failure of endocrine and exocrine glands (hypogonadism, insulin-dependent diabetes mellitus or "bronze diabetes"), cardiac insufficiency, and hair loss.

The object of the invention therefore is to provide pharmaceutical preparations suitable for treatment of haemochromatoses and containing optimum proportions of active substances.

It has unexpectedly been found that erythropoietin preparations in low dosage are suitable for treatment of haemochromatoses.

The invention therefore relates to use of Epo for producing pharmaceutical preparations for treatment of haemochromatoses.

According to the invention the preparations contain 500 to 5000 U of Epo and are preferably used for treatment of patients with secondary haemochromatoses.

The erythropoietin preparations according to the invention can be active substances comparable in physiological effect with human erythropoietin. According to the invention, these active substances will for short be called Epo or Epo-preparations. Recombinant Epo (rhEpo; see European Patent Specifications EP-B1 0 205 564 and EP-B1 0 411 678) or appropriate modifications of these proteins are examples of suitable Epo preparations. The modifications can e.g. be proteins with a molecular weight higher (see EP 0 148 605) or lower than 34000 Da (the SDS-PAGE molecular weight of urinary Epo) or isoforms of the enzyme or protein with varying glycosylation. More particularly, use can also be made of proteins chemically modified by (polyethylene glycol) polyethylene glycol (PEG). In principle, use can also be made of proteins derived by deletion, substitution or prolongation of one or more amino acids in the amino acid sequence of natural Epo having a length of 166 amino acids. The physiological properties of these proteins are substantially comparable with rhEpo. More particularly these proteins have biological properties causing bone marrow cells to increase production of reticulocytes and red blood corpuscles and/or to increase haemoglobin synthesis. Instead of these proteins, use can be made of low-molecular substances called Epo-mimetics, which bond to the same biological receptor. These mimetics can also preferably be administered orally. The preferred amount of these proteins or mimetics is obtained by comparing the biological activity of these active substances with that of Epo.

For use in therapy, the combination preparation according to the invention contains e.g. 500 to 5000 U of an Epo preparation (the abbreviation "U" is an alternative to "IE",= international units). The preferred dosages are 500 U, 1000 U, 2000 U or 5000 U per individual dose.

It has also been found, however, that iron resorption is quantitatively much less important than disturbance in calcium (phosphate) resorption (the concentration ratio is 1:1000) and that a disturbance in calcium (phosphate) resorption is the main factor, apart from disturbance in iron resorption, in primary haemochromatoses.

It has thus been found that on the one hand erythropoiesis is assisted only if transferrin can be fully loaded transferrin ("TF"×2), i.e. if the iron store is full. Otherwise the store is filled with half-loaded transferrin (Tf×1).

On the other hand osteoblasts are supplied with sufficient calcium and phosphate only when the store (bone) is full of hydroxyl apatite. If not, the consequence in the case of iron will be fatal. Too much iron is resorbed, because too much calcium (phosphate) is resorbed. Since Epo is brought to a stop by PTH, erythropoiesis is not assisted.

According to the invention this can be avoided by controlled administration of Epo in low dosage in combination with calcium and/or phosphate compounds.

The invention therefore also relates to use of Epo in low dosage and of calcium and/or phosphate compounds for producing a pharmaceutical preparation for treatment of primary haemochromatoses and a combination preparation consisting of an erythropoietin preparation together with calcium and/or phosphate compounds and suitable for treatment of primary haemochromatosis. The active substances in the combination preparation can be in separate forms of administration or in a single form.

The combination preparation contains optimum proportions of Epo and calcium and/or phosphate for treatment of primary haemochromatosis. According to the invention, in addition to Epo it preferably contains a calcium phosphate complex compound. Particularly preferably it contains an apatite compound having the formula $Ca^{2+}[Ca_3(PO_4)_2]_3^{2-}$, preferably in the form of a gluconate. Alternatively the combination preparation can contain a calcium compound in the form of calcium gluconate and/or a phosphate compound in the form of glucose-1-phosphate or potassium hydrogen phosphate.

The preferred ratio of calcium to phosphate (or phosphorus) in the combination preparation is from 11:5 to 9:7, preferably 10:6.

Alternatively the preparation can contain Epo in combination with a calcium compound only or in combination with a phosphate compound only.

In a preferred variant the combination preparation contains 500–5000 U of recombinant human erythropoietin ("rhEPO"), 20–500 mg calcium and/or 10–250 mg phosphorus (or 30–750 mg phosphate). These values mean that a suitable calcium or phosphate compound must be applied in a quantity such that 20–500 mg calcium or 10 to 250 mg phosphorus (or 30–750 mg phosphate) are supplied.

The combination preparations according to the invention can contain Epo and the calcium and/or phosphate compounds in a unit package ready for sale (known as a combination package). The medicament packs can also contain either a suitable amount of Epo or a suitable amount of a calcium phosphate compound in the form of an individual preparation, the proportion of constituents of the individual preparation in the package being such that they can be administered according to the invention in combination with the respective other preparation. In such cases the manufacturer or importer of the medicament will label the medicament as legally prescribed in many countries, giving instructions or information about the combined administration of the individual preparations. This also applies to medicament packs which contain a suitable amount of Epo and a suitable amount of a calcium compound and/or a phosphate compound.

Calcium or phosphate preparations for oral or parenteral administration are of use according to the invention. In principle the substances can be individual preparations in which the active substance is a physiologically compatible calcium salt and/or a phosphate compound or a calcium phosphate complex compound, or combination preparations which contain the physiologically compatible preparation together with other active substances such as vitamins, folic acid, thiamine chloride, riboflavin, pyridoxine, ascorbic acid or nicotine amide.

Alternatively according to the invention, Epo and calcium and/or phosphate compounds in the form of separate pharmaceutical formulations can be applied simultaneously or successively (free combination). This free combination, which can be provided in a unit pack, has the advantage of great flexibility.

Usually the free combination is supplied in the form of a single unit pack containing at least two containers, the first being an Epo preparation in a suitable form for application (freeze-dried, injection or infusion solution or for oral application if required) whereas the second is the calcium phosphate or calcium and/or phosphate preparation in a suitable form for application. By this means, each patient can individually be provided with the prescribed quantity of Epo and calcium or phosphate compound. These combination preparations have the additional advantage of more successful treatment, since in each case the optimum adjusted amount of the individual preparations is fixed and it is practically impossible to confuse them with other commercial individual preparations on offer in different dosages.

The combination preparations according to the invention also reduce the risk of an accidental excess of calcium and/or phosphate, which might happen if conventional calcium or phosphate preparations from separate packages were applied together with Epo. The combination preparations according to the invention ensure reliable treatment and are easy to handle. Another possibility in the present case is to use one active substance as an injection solution and the other active substance in a form for oral administration.

In the case when the Epo preparation is available in freeze-dried form, the medicament packs (combination packs) contain the appropriate quantity of the Epo preparation in glass ampoules or in capsules. The calcium/phosphate preparation can be in solid form (tablets, powder, granulate, freeze-dried, etc) or in liquid form in separate containers. The combination pack also contains a reconstitution solution for dissolving the freeze-dried Epo, either alone or together with the solid calcium/phosphate preparation. If the calcium/phosphate preparation is in the form of a solution ready for use, the solution can be mixed with the Epo solution if they are to be applied together. Alternatively in principle the calcium/ phosphate preparation can be supplied in concentrated form for addition to conventional infusion solutions, so that application is slower and over a number of hours.

Another possibility according to the invention is to provide individual Epo preparations and calcium and/or phosphate compounds ready for sale in the form of independent medicaments suitable for application, the individual preparations being packaged so as to contain the amounts of individual substances required for the Epo preparation combined with calcium and/or phosphate according to the invention.

Another alternative when using the combination preparations is to administer Epo and calcium and/or phosphate compounds in a "fixed combination", i.e. in a single pharmaceutical formulation containing both compounds. The formulation can e.g. be an injection solution or infusion solution or freeze-dried, e.g. packed into ampoules. A fixed combination of active substances in freeze-dried form has the advantage of simple and safe handling. The freeze-dried substance is dissolved in the ampoule by adding conventional pharmaceutical injection media and is applied intravenously.

The pharmaceutical forms for administration are produced by conventional galenic methods using conventional pharmaceutical adjuvants.

In therapy using the combination preparation according to the invention
(a) the ferritin concentration must be determined, since it is a measure of the level of the iron store,
(b) the transferrin saturation and transferrin receptor must be determined, indicating the loading capacity of the transport protein, and
(c) the level of apatite and collagen in the bone must be determined, using various diagnostic parameters.

The target values, which usually indicate a good adjustment of the iron and bone metabolism, are given in Tables 1 and 2.

TABLE 1

| Diagnosis | |
| --- | --- |
| Ferritin (ng/ml) | ≧100 |
| | Danger limit: 400 |
| Transferrin saturation (%) | ≧15 |
| Soluble transferrin receptor (mg/l) | ≦9 |

TABLE 2

| Analysed substance | Serum [mmol/l] | Serum [mg/dl] | Product Ca × PO$_4$ in Serum [mg/dl]$^2$ | Urine [mmol/l] |
| --- | --- | --- | --- | --- |
| Ca | 2.5 | 10 | 40 | <5 |
| Phosphate | 1 | 4 | | <20 |
| AP, bone | | <150 U/l | | |
| Osteocalcine | | 5–100 μl/l | | |
| Crosslinks | | In urine | | |
| Pyrodinoline | | <100 μmol/mol creatinine | | |
| 3-hydroxy-pyrodinoline | | <20 μmol/mol creatinine | | |
| NTx = N-terminal Crosslinked peptide | | Depends on the method | | |
| PTH | | 10–70 ng/l | | |

Accordingly the following are the main parameters to be checked during therapy:
a) For iron metabolism:
Ferritin (ng/ml)
Transferrin saturation (%) transferrin receptor (mg/l)
The synthesising capacity of the parent cells, based on haemotological control parameters such as haemoglobin (Hb), haematocrit (proportion of red blood corpuscles in the total volume), erythrocytes, hypochromic erythrocytes, reticulocytes, hypochromic reticulocytes.

Ferritin is an iron-storing glycoprotein. Isoferritins typical of tissue exist and can be determined immunologically in the serum. The ferritin value is a measure of the iron stored in the tissue. In most laboratories the normal range is between 30 and 300 ng/ml and the geometrical mean is 88 for men and 49 for women. The serum ferritin values are closely related to the total iron supply in the body. The levels are therefore higher when there is an excess of iron.

In order to determine the ferritin level, erythrocytes are separated from glucocytes and thrombocytes (which also contain ferritin) by centrifuging in blood treated with heparin (or EDTA or citrate). The erythrocytes are then lysed and the stored ferritin is determined immunologically. The erythrocyte ferritin indicates the level of the iron store during the preceding three months (i.e. during the life of an erythrocyte). The normal values are generally between 5 and 48 attograms (ag) per erythrocyte. Values below 5 occur in iron deficiency anaemia whereas elevated values (often >100) occur when there is an excess of iron.

Determination of the serum ferritin is another frequently-used method, e.g. using the Boehringer Mannheim ferritin test, which can be automated and is based on the principle of the immunological agglutination test with amplification of the reaction by latex.

Tranferrin saturation is defined as the ratio of the concentration of iron in the serum/plasma to the concentration of transferrin in the serum plasma (multiplied by a correction factor of 1.41). This number is dimensionless, irrespective of the state of the patient. It is calculated from the formula:

Transferrin saturation (%)=(iron[mg/dl]×100)/(transferrin[m/g/dl]× 1.41)

The serum transferrin receptor can also be determined by the enzyme-intensified immune absorption test (enzyme-linked immunosorbent assay =ELISA) or the latex test, using a monoclonal antibody against the soluble receptor. The reference range is between 0.5 and 3 mg/l.

b) The diagnostic parameters for bone metabolism are as follows:

Ca×PO$_4$ in the serum (in mg/dl)$^2$, and calcium and phosphate in the serum and in the urine (in mmol/l), the level of apatite in the collagen, by determination of bone, apatite ("AP"), pyridinolines ("Crosslinks" and "Crosslabs"), 3-hydroxyproline and N-terminal crosslinked peptide ("NPx"), the concentration of osteocalcine, which can also store and transport apatite. It occurs in the serum in a concentration comparable to that of ferritin (about 10–100 µg/l).

The normal values for calcium and phosphate in the serum are 2.2–2.6 mmol/l corresponding to 8.6–10.2 mg/dl for calcium and 1.0–1.5 mmol/l corresponding to 2.7–4.5 mg/dl for phosphate. This results in a product for Ca×PO$_4$ which can be regarded as acceptable at values between 23 (mg/dl)$^2$(8.6×2.7) and 46 (mg/dl)$^2$(10.2×4.5).

With regard to the composition of the hydroxyl apatite (Ca$_{10}$(PO$_4$)$_6$(OH)$_2$) in the bone, optimum loading capacity occurs at a product Ca×PO$_4$ of about 40 (mg/dl)$^2$ (see Table 3).

TABLE 3

|  | mmol/l |  | mmol/l |
|---|---|---|---|
| Ca$_{serum}$ | 2.2–2.6 | Phosphate$_{serum}$ | 1.0–1.5 |
| Ca$_{apatite}$ | 2.2–2.6 | Phosphate$_{apatite}$ | 1.3–1.6 |

Collagen, the most important protein for storing apatite, is determined indirectly via markers of the bone construction in the serum such as bone ALP and terminal propeptides which split off during formation of collagen fibrils, and via markers of bone disintegration such as pyrodinolines (crosslinks), 3-hydroxy-proline or NTx (N-terminal crosslinked peptides) in the urine.

The serum also contains a concentration of about 10–100 µg/l (normal value) of the matrix protein osteocalcine, which has glutaminic acid radicals enabling it to bond to crystals of the calcium mineral hydroxy apatite incorporated in the bone.

The product calcium×phosphate is the most important quantity in diagnostic investigations and is determined in the serum. It has been found that the bone is sufficiently filled with Ca and PO$_4$ if the product Ca×PO$_4$ is 30–50 (mg/dl)$^2$, the target value being 40 (mg/dl)$^2$. A value above 60 (mg/dl)$^2$ Ca×PO$_4$ indicates calcification of an organ. At values below 25 mg/dl there is a risk of hypocalcaemia or hypophosphataemia, which may result in increased extraction of PTH and cutting-off of Epo.

Accordingly the invention relates to use of Epo in low dosage for producing pharmaceutical preparations for treatment of haemochromatoses. For treatment of secondary haemochromatoses, the preparations contain 500–5000 U of Epo. Treatment is given once to five times, preferably up to four times, a week, without exceeding a total amount of 5000 U Epo per patient per week.

The invention also relates to use of Epo in combination with calcium and/or phosphate compounds for producing combination preparations for treatment of primary haemochromatoses and pharmaceutical combination preparations comprising erythropoietin (Epo) and calcium and/or phosphate compounds, which can be in separate forms for administration or in a uniform form for administration. The following embodiments are particularly important:

Combination preparations containing Epo and a calcium phosphate complex compound. Combination preparations in which the calcium phosphate complex compound is an apatite compound having the formula Ca$^{2+}$[Ca$_3$(PO$_4$)$_2$]$_3^{2-}$, preferably in the form of a gluconate. Combination preparations containing Epo, a calcium and a phosphate compound. Combination preparations in which the phosphate compound is glucose-1-phosphate or potassium hydrogen phosphate. Combination preparations where the ratio of calcium to phosphate is between 11:5 and 9:7, preferably 10:6. Combination preparations containing 500–5000 U Epo, 20–500 mg calcium and/or 10–250 mg phosphorus (or 30–750 mg phosphate) in separate forms for administration as injection or infusion solutions or freeze-dried or in a uniform form for administration.

In therapy using the combination preparation according to the invention, the maximum weekly dosage can be decided in simple manner. Treatment is given one to five times, preferably up to four times a week, the total amount of Epo not exceeding 5000 U and of calcium not exceeding 4×500 mg per patient per week.

To avoid over production of erythrocytes, the treatment may advantageously be accompanied by bloodletting.

The invention also relates to methods of producing pharmaceutical Epo preparations and combination preparations as described hereinbefore, wherein Epo, calcium and/or phosphate compounds are formulated with conventional pharmaceutical excipients or adjuvants and are provided in a uniform or separate forms for administration.

The invention also relates to use of Epo for producing a pharmaceutical preparation for treatment of secondary haemochromatoses and use of Epo and calcium and/or phosphate compounds for producing combination preparations for treatment of primary haemochromatoses.

The invention will now be explained in further detail with reference to examples.

EXAMPLE 1

A patient with primary haemochromatoses and having a ferritin value above 400 ng/ml and a calcium×phosphate value below (20 mg/dl)$^2$ was treated with 1000 U of rhEpo three times a week. The patient was also given 500 mg calcium and 300 mg phosphorus three times a week, preferably in the form of a Ca[Ca$_3$(PO$_4$)$_2$]$_3$ gluconate solution administered orally. The two preparations were given to the patient on the same day. The level of iron in the patient was measured by determining the diagnostic parameters, particularly the transferrin saturation. Treatment was continued until the ferritin and the calcium×phosphate values were in the normal range.

EXAMPLE 2

A patient with secondary haemochromatoses and having a ferritin value above 400 ng/ml was treated with 500 U of rhEpo five times a week. The level of iron in the patient was determined by measuring the transferrin saturation. Treatment was continued until the ferritin value was within the normal range.

What is claimed is:

1. A method for treating primary haemochromatoses in a patient, which comprises administering to the patient a combination therapy comprising (i) an erythropoietin preparation in an amount ranging from 500 to 5,000 U of erythropoietin and (ii) a calcium preparation consisting of 20 to 500 mg of calcium, wherein the erythropoietin preparation and the calcium preparation are each administered from 1 to 5 times weekly with the total amount of erythropoietin administered to the patient not exceeding 5,000 U per week and the total amount of calcium administered to the patient not exceeding 2,000 mg per week, the combination therapy being administered for a period of time sufficient to reduce the severity of the primary haemochromatoses.

2. The method of claim 1, wherein the combination therapy further comprises administering a phosphorus preparation containing from 10 to 250 mg of phosphorus.

3. The method of claim 2, wherein the calcium preparation and the phosphorus preparation are administered as a calcium/phosphate complex.

4. The method of claim 3, wherein the calcium/phosphate complex is an apatite compound.

5. The method of claim 4, wherein the apatite compound has the formula $Ca^{2+}-[Ca_3(PO_4)_2]_3^{2-}$.

6. The method of claim 4, wherein the apatite compound is in the form of a gluconate and wherein the ratio of the calcium to the phosphate in the gluconate form of the apatite compound is from 11:5 to 9:7.

7. The method of claim 6, wherein the ratio is 10:6.

8. The method of claim 3 further comprising monitoring the patient to determine when the target value of Ca×PO$_4$ of amount 40 (mg/dl)$^2$ is reached.

* * * * *